(12) United States Patent
Eckman et al.

(10) Patent No.: US 9,636,384 B2
(45) Date of Patent: May 2, 2017

(54) METHODS FOR MAKING POLYMERIC NANOPARTICLE-POLYPEPTIDE COMPLEX

(75) Inventors: Christopher B. Eckman, Mendham, NJ (US); Aimee R. Herdt, Jacksonville Beach, FL (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 449 days.

(21) Appl. No.: 13/263,052

(22) PCT Filed: Apr. 5, 2010

(86) PCT No.: PCT/US2010/029985
§ 371 (c)(1),
(2), (4) Date: Oct. 5, 2011

(87) PCT Pub. No.: WO2010/117957
PCT Pub. Date: Oct. 14, 2010

(65) Prior Publication Data
US 2012/0040432 A1 Feb. 16, 2012

Related U.S. Application Data

(60) Provisional application No. 61/166,929, filed on Apr. 6, 2009.

(51) Int. Cl.
| | | |
|---|---|---|
| *C12N 9/96* | (2006.01) | |
| *A61K 38/47* | (2006.01) | |
| *A61K 47/48* | (2006.01) | |
| *B82Y 5/00* | (2011.01) | |

(52) U.S. Cl.
CPC ........ *A61K 38/47* (2013.01); *A61K 47/48869* (2013.01); *A61K 47/48907* (2013.01); *A61K 47/48915* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 5,122,614 A * | 6/1992 | Zalipsky | .............. | C07D 207/46 430/363 |
| 5,766,897 A * | 6/1998 | Braxton | ............. | C07K 14/8121 435/188 |
| 5,969,040 A * | 10/1999 | Hallahan | .......... | A61K 47/48215 525/54.1 |
| 8,440,629 B2 * | 5/2013 | Starr et al. | ................... | 514/21.3 |
| 8,546,319 B2 * | 10/2013 | Starr et al. | ........................ | 514/1 |
| 2006/0251726 A1 | 11/2006 | Lin et al. | | |
| 2006/0275371 A1 | 12/2006 | Dai et al. | | |
| 2007/0059775 A1 | 3/2007 | Hultman et al. | | |
| 2008/0014188 A1 | 1/2008 | Zankel et al. | | |

FOREIGN PATENT DOCUMENTS

| | | |
|---|---|---|
| JP | 2002/526383 A | 8/2002 |
| JP | 2009/501237 A | 1/2009 |
| JP | 2009/504042 A | 1/2009 |
| JP | 2009/525744 A | 7/2009 |
| WO | 95/03357 | 2/1995 |
| WO | WO-95/03357 A1 | 2/1995 |
| WO | 9959548 | 11/1999 |
| WO | WO-99/59548 A1 | 11/1999 |
| WO | 03000778 | 1/2003 |
| WO | 2006108052 | 10/2006 |
| WO | 2007034479 | 3/2007 |
| WO | 2007/091159 A2 | 8/2007 |
| WO | WO-2007/091159 A2 | 8/2007 |
| WO | WO-2007/149062 A2 | 12/2007 |
| WO | 2008091465 | 7/2008 |
| WO | 2008105773 | 9/2008 |

OTHER PUBLICATIONS

Duncanson et al. (Biomaterials, vol. 28, 2007, pp. 4991-4999).*
Luzi et al. (Genomics, vol. 26, 1995, pp. 407-409).*
Kinstler (Advan. Drug Reviews, vol. 54, 2002, pp. 477-485).*
International Preliminary Report on Patentability for PCT/US2010/029985, 5 pages (Oct. 11, 2011).
International Search Report for PCT/US2010/029985, 3 pages (Jan. 3, 2011).
Written Opinion for PCT/US2010/029985, 4 pages (Jan. 3, 2011).
Second Official Notification of Defects in Israeli Patent Application No. 215455, National Phase of PCT/US10/029985, "Methods and Materials for Delivering Molecules", dated Nov. 24, 2015.
First Official Notification of Defects in Israeli Patent Application No. 215455, National Phase of PCT/US10/029985, "Methods and Materials for Delivering Molecules", dated Feb. 9, 2014.
Official Notification of Examination Search Report in Canadian Patent Application No. 2,757,645, National Phase of PCT/US10/029985, "Methods and Materials for Delivering Molecules", dated Feb. 4, 2016.
International Search Report for PCT/US10/029985, "Methods and Materials for Delivering Molecules", dated Jan. 3, 2011.
Official Action in Japanese Patent Application No. 2012-503772, National Phase of PCT/US10/029985, "Methods and Materials for Delivering Molecules", dated Jun. 2, 2015.
Ataman-Onal, Y. et al. "Surfactant-free anionic PLA nanoparticles coated with HIV-1 p24 protein induced enhanced cellular and humoral immune responses in various animal models." Journal of Controlled Release. vol. 112, No. 2, May 15, 2006. pp. 175-185.
Farokhzad, O.C. et al. "Nanoparticle-aptamer bioconjugates: a new approach for targeting prostate cancer cells." Cancer Research, American Association for Cancer Research. vol. 64, No. 21, Nov. 1, 2004, pp. 7668-7672.
Olivier, Jean-Christopher et al., "Synthesis of pegylated immunonanoparticles." Pharmaceutical Research, Vo. 19, No. 8, Aug. 1, 2002, pp. 1137-1143.

(Continued)

*Primary Examiner* — Hope Robinson
(74) *Attorney, Agent, or Firm* — Gearhart Law, LLC

(57) ABSTRACT

This document relates to methods and materials involved in delivering molecules to a mammal. For example, methods and materials for using nanoparticles to increase the half-life and the bioavailability of molecules administered to a mammal are provided.

19 Claims, 8 Drawing Sheets

(56) References Cited

OTHER PUBLICATIONS

Gao et al. "UEA I-bearing nanoparticles for brain delivery following intranasal administration." International Journal of Pharmaceutics. vol. 340, No. 12, Jul. 19, 2007, pp. 207-215.

Gao et al. "Lectin-conjugated PEG-PLA nanoparticles: Preparation and brain delivery after intranasal administration." Biomaterials, vol. 27, No. 18, Jun. 1, 2006, pp. 3482-3490.

Extended European Search Report for European Application No. 1076266.4. Mailed Apr. 7, 2015. 13 pages.

* cited by examiner

METHODS FOR MAKING POLYMERIC NANOPARTICLE-POLYPEPTIDE COMPLEX

CROSS-REFERENCE TO RELATED APPLICATIONS

The present application claims priority under 35 U.S.C. 371 to International Application No. PCT/US2010/029985, filed on Apr. 5, 2010, which claims the benefit of priority to U.S. Provisional Application Ser. No. 61/166,929, filed on Apr. 6, 2009. The entire contents of each of the above-referenced applications are incorporated herein by reference.

BACKGROUND

1. Technical Field

This document relates to methods and materials involved in delivering molecules to a mammal. For example, this document provides methods and materials for using nanoparticles to increase the half-life or the bioavailability of molecules administered to a mammal.

2. Background Information

Methodologies have been developed for treating a variety of medical disorders with the administration of molecules including, for example, polypeptides, small peptides, antibodies, short interfering RNAs (siRNAs), and anti-cancer, anti-viral, and antibiotic medicaments. The efficacy of such treatments can be limited by the presence of substances which degrade molecules upon delivery to the body. For example, proteases and other endogenous enzymes can degrade polypeptides administered during enzyme replacement therapy to treat conditions characterized by the absence or disruption of normal enzymatic function.

SUMMARY

This document provides methods and materials for delivering molecules to a mammal. This document is based, in part, on the discovery of methods to increase the half-life of molecules administered to a mammal. For example, this document provides methods and materials for increasing the half-life or bioavailability of enzymes, polypeptides, peptide fragments, nucleic acids, and other molecules using nanoparticles. In some cases, the methods and materials provided herein can be used to improve delivery across the blood brain barrier. This document also provides methods and materials for delivering molecules to a mammal for treating conditions characterized by the absence or disruption of normal enzymatic function. For example, the methods and materials provided herein can be used to treat degenerative neurological disorders by increasing enzyme levels in the central nervous system. In some cases, the methods and materials provided herein can be used by clinicians or other professionals to treat humans afflicted with Krabbe disease or other lysosomal storage disorders by increasing therapeutic enzyme delivery across the blood brain barrier.

In general, one aspect of this document features a composition. The composition comprises, or consists essentially of, a polypeptide having enzymatic activity attached to a polymeric nanoparticle. The polypeptide can have a longer half life in human serum than a control polypeptide having an enzymatic activity and not attached to a nanoparticle. The polypeptide can have at least 85 percent of the level of an enzymatic activity of a control polypeptide not attached to a nanoparticle. The polypeptide can have at least 95 percent of the level of an enzymatic activity of a control polypeptide not attached to a nanoparticle. The polypeptide can have the same level of an enzymatic activity of a control polypeptide not attached to a nanoparticle. The polypeptide can be a galactocerebrosidase polypeptide. The polymeric nanoparticle can be assembled from COOH-PEG-PLA, methoxy-PEG-PLA polymers, maleimide-PEG-PLA polymers, or any combination thereof. The polypeptide can be attached to a polymeric nanoparticle via a covalent bond. The polypeptide can be attached to a polymeric nanoparticle via a non-covalent bond. The polypeptide can be attached to a nanoparticle via the N- or C-terminus of a polypeptide.

In another aspect, this document features a method for increasing the half life of a polypeptide having enzymatic activity in serum. The method comprises, or consists essentially of, attaching a polypeptide to a polymeric nanoparticle to form a complex. The attached polypeptide can have a longer half life in serum than a control polypeptide having an enzymatic activity and not attached to a nanoparticle. The polypeptide attached to a nanoparticle can have at least 85 percent of the level of an enzymatic activity of a control polypeptide not attached to a nanoparticle. The polypeptide attached to a nanoparticle can have at least 95 percent of the level of an enzymatic activity of a control polypeptide not attached to a nanoparticle. The polypeptide attached to a nanoparticle can have the same level of an enzymatic activity of a control polypeptide not attached to a nanoparticle. The polypeptide can be a galactocerebrosidase polypeptide. The polymeric nanoparticle can be assembled from COOH-PEG-PLA, methoxy-PEG-PLA polymers, maleimide-PEG-PLA polymers, or any combination thereof. The polypeptide can be attached to a polymeric nanoparticle via a covalent bond. The polypeptide can be attached to a polymeric nanoparticle via a non-covalent bond. The polypeptide can be attached to a nanoparticle via the N- or C-terminus of the polypeptide.

In another aspect, this document features a method for increasing the stability of a polypeptide having enzymatic activity. The method comprises, or consists essentially of, attaching a polypeptide to a polymeric nanoparticle to form a complex. The attached polypeptide can have greater stability than a control polypeptide having an enzymatic activity and not attached to a nanoparticle. The polypeptide attached to a nanoparticle can have at least 85 percent of the level of enzymatic activity of a control polypeptide not attached to a nanoparticle. The polypeptide attached to a nanoparticle can have at least 95 percent of the level of enzymatic activity of a control polypeptide not attached to a nanoparticle. The polypeptide attached to a nanoparticle can have the same level of enzymatic activity of a control polypeptide not attached to a nanoparticle. The polypeptide can be a galactocerebrosidase polypeptide. The polymeric nanoparticle can be assembled from COOH-PEG-PLA, methoxy-PEG-PLA polymers, maleimide-PEG-PLA polymers, or any combination thereof. The polypeptide can be attached to a polymeric nanoparticle via a covalent bond. The polypeptide can be attached to a polymeric nanoparticle via a non-covalent bond. The method can further comprise lyophilizing a complex to form a lyophilized complex. The polypeptide can be attached to a nanoparticle via the N- or C-terminus of a polypeptide.

In a further aspect, this document features a method of reducing nanoparticle aggregation. The method comprises, or consists essentially of, attaching a polypeptide to a polymeric nanoparticle via the N- or C-terminus of the polypeptide to form a complex, wherein a preparation of complexes exhibit less nanoparticle aggregation than a control preparation having polymeric nanoparticles not attached to a polypeptide via the N- or C-terminus of a polypeptide.

The polypeptide can be a galactocerebrosidase polypeptide. The polymeric nanoparticle can be assembled from COOH-PEG-PLA, methoxy-PEG-PLA polymers, maleimide-PEG-PLA polymers, or any combination thereof. The polypeptide can be attached to a polymeric nanoparticle via a covalent bond. The polypeptide can be attached to a polymeric nanoparticle via a non-covalent bond. The method can further comprise lyophilizing a complex to form a lyophilized complex.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
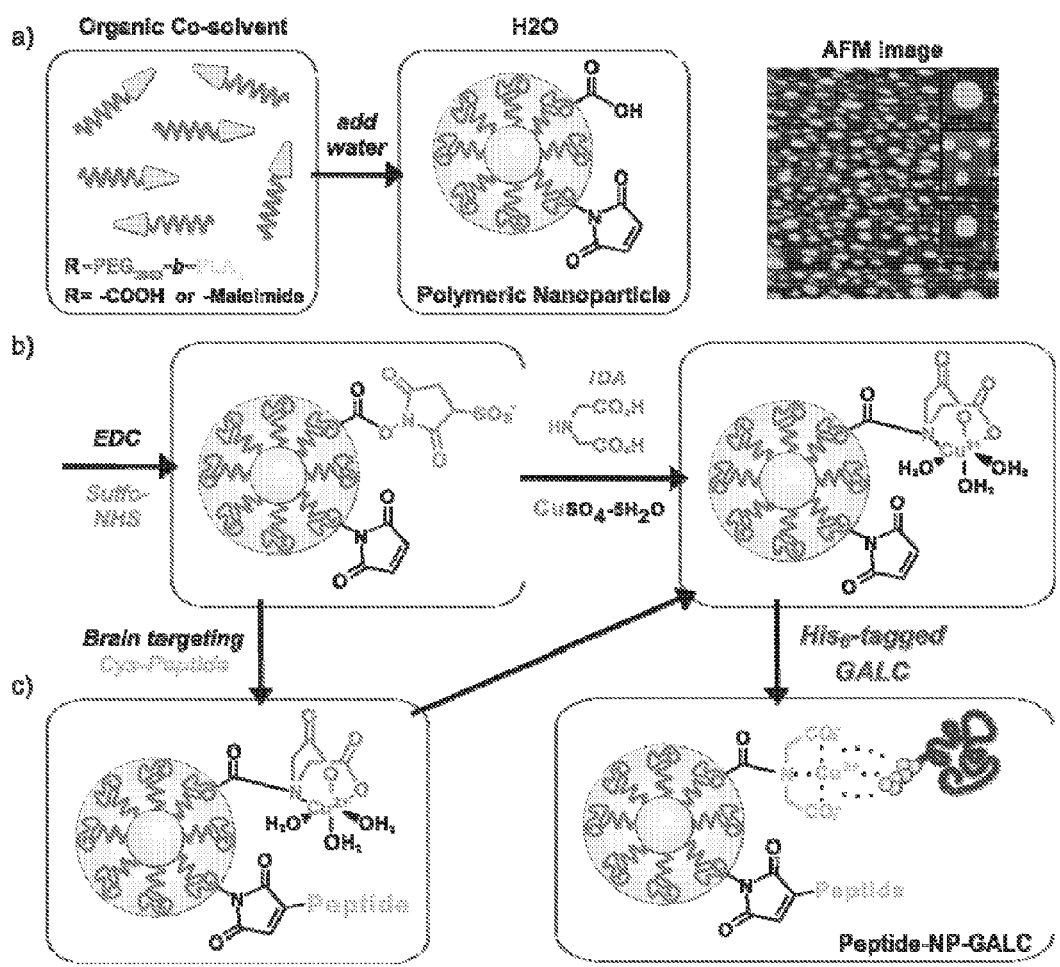
FIG. 1 depicts a strategy for nanoparticle synthesis and for covalent attachment of GALC. (A) 10 mg each of the diblock copolymer surfactants, COOH-PEG-PLA and methoxy-PEG-PLA (or maleimide-PEG-PLA) were dissolved in 2 mL dichloromethane. Following the flash addition of 10 mL of water and repetitive emulsion (vortex/sonication), the copolymers self-assembled into micelles. AFM images were collected on a Nanoscope III controller with a Multimode AFM (Veeco Instruments, Inc.) set to ambient tapping mode and collecting data over a 100 µm$^2$ area. Scale bars in all AFM images are set to 30 nm. (B) Carboxylic functional groups (—COOH) were converted into activated esters, followed by interaction with IDA, and $Cu^{2+}$ activation. Finally, $Cu^{2+}$–IDA NPs were incubated His6-tagged GALC. (C) Scheme for attaching cysteine-containing peptides to maleimide functional groups on the NP surface.

This document provides methods and materials related to delivering molecules to a mammal. For example, this document provides methods and materials for attaching enzymes and other molecules to nanoparticles. As described herein, such nanoparticles can be used to increase physiological concentrations, to prolong bioavailability, and to improve delivery across the blood brain barrier of enzymes and other molecules upon administration to a mammal. In some cases, compositions of nanoparticles exhibiting such improved properties can be used for delivering molecules to a mammal for treating conditions characterized by the absence or disruption of normal enzymatic function. As used herein, "bioavailability" refers to the concentration of a molecule (e.g., enzyme, peptide) available for delivery to and uptake by a cell, tissue, or biological compartment. As used herein, increased and/or prolonged bioavailability refers to a compound's enhanced capacity to be delivered to or taken up by a cell, tissue, or biological compartment (e.g., enhanced absorption into the blood, enhanced delivery to the brain).

With conventional manufacturing methods, a significant amount of agent (e.g. biopharmaceutical, enzyme, antibody) yield can be lost due to agglomeration or aggregation of agent and degradation. To compensate for and/or to avoid aggregation and degradation problems, conventional methods include the addition of various excipients to agent compositions. The addition of numerous excipients, however, can be adverse to patient outcomes. Poly-ethylene glycol (PEG) is an example of an excipient used in the manufacture of enzymes. PEG is added to the agent/enzyme in a indiscriminate manner, that is, the PEG is added/attached to the enzyme at random sites along the enzyme. The methods and materials provided herein can include having the agent/enzyme conjugated to nanoparticles (e.g. the PEG-PLGA copolymer described herein) with the nanoparticles conjugated to either the N- or C-terminus of the enzyme (or, in some cases, an antibody, polypeptide, or peptide). In some cases, conjugating nanoparticles to the N- or C-terminus of a polypeptide (e.g., an enzyme) can substantially reduce aggregation, can result in the polypeptide's activity (e.g., enzymatic activity) remaining unaffected, and can be used in a process having a nanoparticle yield that is effective. Nanoparticles produced by the methods provided herein can display greatly increased stability in solution, during storage, and upon lyophilization and resuspension. As such, nanoparticles produced by the methods provided herein can have substantial clinical value.

As used herein, the terms "stable" and "stability" refer to the ability of agent-nanoparticle compositions (e.g., polymeric nanoparticles) to remain substantially unchanged. One measure of agent-nanoparticle stability is the ability of an agent-nanoparticle composition not to agglomerate and/or to form aggregates over time. Another measure of agent-nanoparticle stability is the ability of an agent-nanoparticle composition not to degrade over time. Agent-nanoparticles having increased stability are less likely to substantially form aggregates and/or to substantially degrade over time (e.g., during manufacture, during storage, or in solution).

As used herein, the term "treat" means to decrease, suppress, attenuate, diminish, arrest, or stabilize the development or progression of a disease or disorder delineated herein (e.g., a lysosomal storage disorder), lessen the severity of the disease or disorder, or lessen the severity of or improve the symptoms associated with the disease or disorder.

As used herein, the term "prevent" refers to reducing the likelihood of developing a disease or disorder delineated herein (e.g., developing symptoms associated with a lysosomal storage disorder), or reducing the likelihood of the recurrence of a disease or disorder delineated herein (e.g., experiencing recurrent symptoms associated with a lysosomal storage disorder).

The nanoparticles provided herein can be polymeric nanoparticles. Polymers synthesized by any appropriate method can be used for polymeric nanoparticle assembly. In some cases, polymers appropriate for the nanoparticles provided herein can be synthesized using a ring-opening polymerization (ROP) protocol. For example, polymer synthesis can be ring-opening polymerization performed according to previously described protocols (see Zhang et al., *Colloid Polym. Sci.* 282:1323-8 (2004); Dong and Feng, *Biomaterials*, 25(14):2843-9 (2004); Zhang et al., *J. Drug Target* 14(5): 281-90 (2006)).

The nanoparticles provided herein can be assembled from a mixture of polymers. For example, polymeric nanoparticles can be assembled from a mixture of COOH-PEG-PLA and methoxy-PEG-PLA polymers. In some cases, polymeric nanoparticles can be assembled from a mixture of COOH-PEG-PLA and maleimide-PEG-PLA polymers. Other polymers suitable for assembly of the nanoparticles provided herein can include poly(lactic-co-glycolic acid) (PLGA), poly(acrylic acid) (PAA), poly(butyl cyanoacrylate) (PBCA), poly(vinyl alcohol) (PVA), poly(vinyl acetate), poly(ethylene oxide) (PEO), polystyrene (PS) and polyethyleneimine (PEI). Polymeric nanoparticles can be assembled according to any appropriate method. In some cases, nanoparticles can self-assemble into core and shell structures from individual amphipathic polymers containing both hydrophobic and hydrophilic portions to form solid, colloidal, and highly soluble nanoparticles. Other suitable methods for nanoparticle assembly can include emulsification, sonnication, dropwise solvent addition, and reverse micelle method.

Molecules can be conjugated to the surface or the core of a polymeric nanoparticle by covalent interactions, non-covalent interactions (e.g., chelation), electrostatic interactions, adsorption, or simple binding. Conjugating an enzyme, polypeptide, or other molecule to a nanoparticle as described herein can increase the half-life of the attached molecule in vivo or in vitro. For example, poly(ethylene glycol) (PEG) nanoparticles can increase the systemic circulation half-life of an attached therapeutic molecule by protecting the therapeutic cargo from enzymatic degradation and by preventing premature uptake by the reticuloendothelial system. In some cases, nanoparticles can increase the half-life of an attached therapeutic molecule in serum, blood, plasma, or in the human body relative to the half-life of a therapeutic molecule in its unbound state in serum, blood, plasma, or in the human body. In some cases, poly(lactide) (PEG-b-PLA), which is a biocompatible and biodegradable polymer, can be used to form a nanoparticle core. Polymeric nanoparticles formed from a diblock copolymer (e.g., poly(ethylene glycol)-block-poly(lactide)) can be stable and biologically compatible. Such nanoparticles can biodegrade to release a conjugated enzyme or other cargo with an increased half-life in vivo. For example, enzymes released following nanoparticle biodegradation can be detected in the circulatory system more than 24 hours after intravenous injection.

Any appropriate biomolecule can be conjugated to the surface or the core of a polymeric nanoparticle. For example, an enzyme (e.g., an endogenous enzyme or a recombinant enzyme), polypeptide, antibody, peptide nucleic acid (PNA), siRNA, oligonucleotide, or small molecule can be conjugated to a polymeric nanoparticle for delivery of the biomolecule to a mammal. In some cases, more than one biomolecule can be conjugated to the surface or the core of a nanoparticle. For example, nanoparticles can be simultaneously decorated with therapeutic cargo and cellular- or organ-targeting molecules such as peptides, antibodies, oligonucleotides, small molecules, and other macromolecules that specifically recognize certain cells or organs. As a result, such heterofunctionalized nanoparticles can be delivered to specific in vivo locations upon administration to a mammal. In some cases, cell-penetrating peptides (CPPs) can be fused to other therapeutic cargo (e.g., therapeutic enzymes, polypeptides, oligonucleotides) to enhance translocation of the nanoparticles provided herein across cell membranes and to promote delivery of such therapeutic agents to a target cell, tissue, or biological compartment. In some cases, a polypeptide inhibitor such as TIMP-1 can be conjugated to the surface or the core of a polymeric nanoparticle for delivery of the polypeptide inhibitor to a mammal. In some cases, nanoparticles provided herein can have other surface chemical moieties. For example, a surface chemical moiety can be a carboxylic acid, hydroxyl, maleimide, amine, methoxy, amino acid, NHS ester, NHS, sulfhydryl (thiol), carbamate, alkyl halide, iminodiacetic acid ($Cu^{2+}$), or nitrotriacetic acid ($Ni^{2+}$).

In some cases, the nanoparticles provided herein can be lyophilized. Any appropriate method can be used to form lyophilates. For example, lyophilates can be formed by lyophilization (freeze-drying), nitrogen purging, or centrifugal vacuum concentration. In some cases, excipients can be used during lyophilization by any of the methods described herein. Any appropriate excipient can be used such as, for example, methyl cellulose, cyclodextrin, polyethylene glycol, hydroxypropyl cyclodextrin, and surfactants (e.g., polyoxyethyleneglycol dodecyl ether (Brij 35) or sodium dodecyl sulfate). Excipients can be used in the range of, for example, about 0.5 to about 10%. Lyophilized nanoparticles can be used immediately, or stored for later use (e.g., stored for use about 1 day, 1 week, 1 month, 2 months, 3 months, 4 months, 5 months, or 6 months later). Storage can be, for example, at any appropriate temperature (e.g., 4° C.) under any appropriate conditions (e.g., dry storage). In some cases, lyophilized nanoparticles can be stored for later use without an increase in nanoparticle size e.g., by the formation of nanoparticle aggregates, and/or without a loss of enzymatic activity. In some cases, lyophilates of the nanoparticles provided herein can be reconstituted prior to use. For example, lyophilized nanoparticles can be reconstituted in a solution (e.g., water or a buffered solution) prior to use.

The nanoparticles provided herein can be administered to a mammal for any appropriate therapeutic purposes. For example, nanoparticles can be administered to a mammal for enzyme placement therapy or for anti-cancer, anti-viral, or antibiotic therapies. In some cases, the nanoparticles provided herein can be administered to a mammal in order to deliver molecules to a target cell, tissue, or biological compartment. For example, the nanoparticles provided herein can be used to increase delivery of biomolecules (e.g., a polypeptide, antibody, peptide, siRNA, or oligonucleotide) or chemical moieties (e.g., a carboxylic acid, hydroxyl, or malemide) when such molecules are conjugated to the nanoparticle surface or core. The type of cargo to be attached to a nanoparticle can depend on the type of therapeutic regimen for which the nanoparticles are to be administered to a mammal. For example, enzymes can be conjugated to the surface or the core of a polymeric nanoparticle to deliver such enzymes to a mammal having a condition characterized by the absence of a functional enzyme or the presence of a dysfunctional enzyme. Such therapeutic regimens can be used to treat or prevent diseases such as, for example, Krabbe disease, Type I Gaucher's disease, Fabry's disease, Hurler syndrome, Niemann-Pick B disease, Pompe disease, Farber disease, San Filippo syndrome, or Tay-Sachs disease. Other therapeutic regimens for which the nanoparticles are suitable can include, for example, anti-cancer, anti-viral, and antibiotic therapies. For treating cancer, small molecules with chemotherapeutic properties can be attached to a nanoparticle for use according to the methods described herein. For treating viral and bacterial infections, small molecules or peptides with anti-viral and antibiotic properties, respectively, can be conjugated to nanoparticles for use according to the methods described herein. In some cases, the attachment of a potentially therapeutic molecule to a nanoparticle can increase the therapeutic efficacy of the molecule and/or reduce unwanted side effects when compared to administration of the molecule alone.

Any appropriate mammal can be treated with the methods and materials provided herein. For example, humans, non-human primates, horses, cows, pigs, dogs, cats, guinea pigs, rats, mice, and rabbits can be treated with the methods and materials provided herein. A nanoparticle can be used to deliver a molecule to any appropriate target in the body of a mammal. For example, a nanoparticle-molecule complex can be targeted to any organ, tissue, cell, organelle, or biomolecule (e.g., a nucleic acid or polypeptide) in the body of a mammal in order to localize enzymatic or pharmacological activity to a particular site or tissue. A nanoparticle provided herein can be administered to any part of a mammal's body. For example, a nanoparticle can be administered to a body cavity, an organ, a body part, or a body fluid.

Any appropriate concentration of nanoparticles can be administered to a mammal. For example, nanoparticles can be administered to a mammal at a concentration of about 0.1 mg/kg to about 1000 mg/kg. In some cases, nanoparticles can be heterofunctionalized to co-administer two or multiple compounds simultaneously. In some cases, nanoparticles can be suspended in a solution to facilitate administration of the nanoparticles to a mammal. For example, nanoparticles can be suspended in tris-, phosphate- or carbonate-based buffers, water, saline, a surfactant-containing solution, a dimethylsulfoxide-containing solution, or an emulsion forming solution including, without limitation, methylcellulose. Any appropriate mode of administration can be used. For example, nanoparticles provided herein can be administered to a mammal by intravenous (i.v.), intraperitoneal (i.p.), or intracerebroventricular (i.c.v.) injection. The nanoparticles provided herein can be administered to a mammal by other routes, e.g., intramuscularly, subcutaneously, sublingually, intrathecally, or intradermally. The route of administration can depend on a variety of factors, such as the therapeutic goals.

In some cases, the methods and materials provided herein can increase or prolong the bioavailability of a target molecule in a mammal. Improved bioavailability of an enzyme or other molecule can be evaluated relative to a control composition. For example, a molecule attached to a nanoparticle can exhibit improved or prolonged bioavailability in vivo as compared to the molecule when it is not attached to a nanoparticle. For example, a loaded molecule could have reduced bioavailability as compared to a molecule that is not conjugated onto a nanoparticle can be determined by methods known to those of ordinary skill in the art. For example, bioavailability of a molecule in serum can be assessed by determining the peak plasma drug concentration, time of peak drug concentration, and area under the plasma concentration—time curve. Other assays for measuring molecule bioavailability in biological samples are known in the art (Wrobel et al., *Biol. Trace Element Res.* 68(2):97-106 (1999); Motzok et al., *J. Assoc. Anal. Chem.* 61(4):887-93 (1978); Johnson, *Biol. Trace Element Res.* 19:3-10 (1989); Hazel et al., *British J. Nutr.* 57:223-33 (1987); Oomen et al., *Environ. Sci. Tech* 35:3326-34 (2002)).

This document also provides methods and materials related to treating enzymatic disorders or increasing enzyme levels in a mammal using enzyme replacement therapy. Enzymatic disorders can be caused by genetic defects that partially or completely abolish enzymatic activity of a polypeptide. Enzyme replacement therapy is a form of medical intervention that replaces an enzyme in a subject in which the particular enzyme is deficient or absent. Exemplary enzymatic disorders that can be treated using the methods and materials provided herein include, without limitation, phenylketonuria (PKU), sickle cell anemia, cystic fibrosis, and mitochondrial disorders which manifest in some patients with Autism spectrum disorders. In some cases, the nanoparticles provided herein can have functional enzymes as cargo. Such nanoparticles can restore or improve enzymatic function in a mammal when administered as described herein.

In some cases, the methods and materials provided herein can be used to increase enzyme levels in the central nervous system and to provide enzyme replacement therapy to treat degenerative neurological disorders. For example, the nanoparticles provided herein can be used to treat a degenerative neurological disorder such as a lysosomal storage disorder in a mammal. In some cases, the lysosomal storage disorder is Krabbe disease. Other lysosomal storage disorders that can be treated using the methods and materials provided herein can include, without limitation, Type I Gaucher's disease, Fabry's disease, Hurler syndrome, Niemann-Pick B disease, Pompe's disease, Farber disease, San Filippo syndrome, or Tay-Sachs disease. For use of the nanoparticles provided herein for enzyme replacement therapy for the treatment of degenerative neurological disorders, any appropriate molecule can be conjugated to the surface or the core of a nanoparticle (e.g., a polymeric nanoparticle). For example, an enzyme, polypeptide, antibody, peptide fragment, PNA, short interfering RNA (siRNA), oligonucleotide, or small molecule can be conjugated to a polymeric nanoparticle for delivery of the molecule to a mammal. In some cases, the molecule can be a peptide or polypeptide. In some cases, a polypeptide inhibitor such as TIMP-1 can be conjugated to the surface or the core of a nanoparticle (e.g., a polymeric nanoparticle) for delivery of the polypeptide inhibitor to a mammal.

For the treatment of degenerative neurological disorders, enzymes associated with the disorder can be conjugated to the surface or the core of a nanoparticle (e.g., a polymeric nanoparticle). An exemplary enzyme for the methods and materials provided herein is galactocerebrosidase (GALC), which can be absent or dysfunctional in some lysosomal storage disorders. Other enzymes suitable for the methods and materials provided herein can include, without limitation, beta-glucosidase (associated with Gaucher disease types I, II, and III), alpha-galactosidase A (associated with Fabry's disease), ceramidase (associated with Farber disease), alpha-L-iduronidase (associated with Hurler syndrome), maltase (associated with Pompe's disease), sphingomyelinase (associated with Niemann-Pick B disease), hexosaminidase (associated with Tay-Sachs disease), sulfamidase (SGSH) (associated with San Filippo syndrome, or mucopolysaccharidosis III), and arylsulfatase A (ARSA) (associated with metachromatic leukodystrophy).

Experiments can be performed to determine whether molecules are successfully delivered to a target cell, tissue, or biological compartment. For example, any appropriate assay can be performed to determine whether administration of a nanoparticle provided herein increased physiological concentration or prolonged bioavailability of the enzymes or other molecules conjugated to such nanoparticles. In some cases, assays can be performed to determine whether there was successful enzyme replacement therapy upon administration of a nanoparticle provided herein. Successful enzyme replacement therapy can be determined by assessing the biodistribution of conjugated enzymes and by evaluating histopathology in treated mammals. Other appropriate methods of determining successful delivery of molecules to a mammal can include Western blotting using antibodies directed against enzymes or other polypeptides conjugated to nanoparticles, ELISA, functional assays of enzymatic activity, and assays to detect decreased proteolysis of an enzyme. Decreased proteolysis of the target molecule can be indicative of increased bioavailability of the molecule. Other assays that can be used to detect molecule delivery and bioavailability can include biophysical methods, spectroscopy, microscopy, and cellular and tissue imaging.

Any appropriate method can be used to determine successful treatment of a neurological condition upon administration of the nanoparticles provided herein. In some cases, localization of GALC to the brain can be detected. In some cases, subcellular localization of GALC can be detected in Schwann cells, hepatocytes, and kidney cuboidal cells. The affinity-purified anti-GALC polyclonal antibody CL1475 or the anti-GALC monoclonal antibody raised against recombinant human GALC protein can be used for localization assays. In some cases, an increase in GALC enzymatic activity as determined by increased levels of cleavage product can be detected in brain homogenates. For example, brain homogenates can be analyzed by a GALC substrate turnover reaction. Reduced accumulation of psychosine, a cytotoxic GALC substrate, can be detected by mass spectral analysis in the brains, and more particularly in myelin-forming cells such as oligodendrocytes and Schwann cells, of treated mammals. Successful enzyme replacement therapy by the methods provided herein can reduce demyelination of sciatic nerve. In some cases, an increased number of oligodendrocytes can be detected following administration of the nanoparticles provided herein. In some cases, reductions in axonal loss, astrocytic gliosis, and infiltration of multinucleated peripheral macrophages or "globoid cells" can be observed. Successful enzyme replacement therapy can also be determined by an improvement in the clinical phenotype in treated mammals (e.g., an improvement in spasticity, irritability and hypersensitivity to external stimuli, opisthotonic posturing, visual failure, hypertonic fits, or loss of tendon reflexes).

The invention will be further described in the following examples, which do not limit the scope of the invention described in the claims.

EXAMPLES

Example 1

Peripheral Administration of GALC

Weekly intraperitoneal (i.p.) injections of recombinant murine GALC, harvested from GALC transfected HEK293 cells and purified by affinity chromatography, were performed on twitcher mice beginning at PND 10 or 20. These dosing regimens were selected to mimic both pre- and post-development of the twitcher neuropathology. The naturally occurring mouse model, twitcher, is enzymatically authentic to Krabbe disease. The twitcher mice phenotype derives from a single G>A mutation in the GALC gene, which produces an inactive form of GALC and causes demyelination in the CNS and peripheral nervous system by post-natal day (PND) 20. Twitcher mice typically succumb to their disease state around PND 40-42, after experiencing a failure to thrive, limb weakness and paralysis, and involuntary head twitching. Both enzyme replacement therapy (ERT) treatments equally increased the twitcher mouse life span from approximately 41 to 46 days, which is likely a clinically significant improvement considering the rapid and aggressive pathological deterioration of these mice compared to that of humans. Biodistribution studies showed the enzyme localized almost exclusively to the periphery, particularly in the liver. However, low levels of recombinant GALC were detected in brain both by enzymatic activity and by immunohistochemical methods. Collectively, this data indicate that peripheral ERT has potential as a treatment for Krabbe disease but that increased blood brain barrier (BBB) penetrance and longer enzyme half-life would likely improve clinical outcome.

In a separate study, twitcher mice that received a single unilateral injection of recombinant GALC showed widespread enzyme distribution in the brain including regions distal to the injection site. Animals receiving a single intracerebroventricular (i.c.v.) injection dose of GALC at PND 20 survived up to 52 days, which compares favorably to the control twitcher animals that only live to approximately PND 40-42. While single dose i.c.v. injection is clinically feasible, it is considerably more invasive than i.p. or i.v. dosing. Therefore, GALC administration by chronic i.c.v. based treatment is unlikely. Nonetheless, these data suggests that if GALC's BBB penetrance is increased, there will be a more positive clinical impact.

A pseudo-ELISA based method was developed to quantify GALC activity in the plasma. First, adsorbent plates (Nunc Maxisorp) were coated with an affinity-purified chicken anti-GALC antibody (U1021). Plasma samples were processed using standard methods and EDTA, then directly added to the plates, where GALC was allowed to bind. Following extensive washing, a GALC colorimetric substrate in its reaction buffer was added. The reaction was stopped at a defined interval and the absorbance read by plate reader (Molecular Devices). Using known amounts of GALC spiked into twitcher mouse plasma (no GALC) as a standard curve on the same plates, GALC levels in the plasma were reliably quantified.

Example 2

PEG-b-PLA Nanoparticle Synthesis

The small sizes of nanoparticles (2-100 nm) make them suitable for use in biological systems. The large surface-to-volume ratio is amenable to encapsulation or functionalization with similarly sized biomolecules, such that several copies of the same biomolecule can be loaded into single NP cores or conjugated to NP surfaces. Polymeric NPs self-assemble into core/shell structures from individual amphipathic polymers (containing both hydrophobic and hydrophilic portions); forming solid, colloidal, highly soluble NPs. In order to improve GALC biostability and bioavailability for the central nervous system, polymeric PEG-b-PLA NPs selectively conjugated to GALC were synthesized. The diblock copolymer, PEG-b-PLA was synthesized as previously described (Zhang et al., *Colloid Polym. Sci.* 282:1323-8 (2004); Dong and Feng, *Biomaterials*, 25(14): 2843-9 (2004); Zhang et al., *J. Drug Target* 14(5):281-90 (2006)), with slight modification. Briefly, double-distilled D,L-lactide was polymerized onto R-PEG3500-OH using a one-pot, ring-opening polymerization (ROP) reaction, where R represents methoxy, carboxyl or maleimide moieties (FIG. 1A). ROP proceeded for 48 hours at 130° C. under inert atmosphere, which was determined to be the best conditions for generating similarly sized PEG- and PLA-polymer blocks. Reactions and final polymer sizes were monitored by NMR. NPs were self-assembled by a co-solvent emulsion approach using different ratios of the methoxy-, carboxyl- and maleimide-terminated polymers. NPs were characterized by atomic force microscopy (AFM) and estimated to be approximately 30 nm in diameter (FIG. 1A). PEG-carboxylates on the NP surface were selectively converted to iminodiacetic acid (IDA) using carbodiimide (EDC) coupling chemistry, then mixed with His6-tagged GALC which is captured to the NP surface through standard immobilized metal affinity chromatography, to form NP-GALC conjugates (FIG. 1B). After NP functionalization, conjugates are subjected to extensive dialysis and high speed centrifugation to remove any excess reagents (including unbound GALC) (FIG. 1C).

Figure 2:
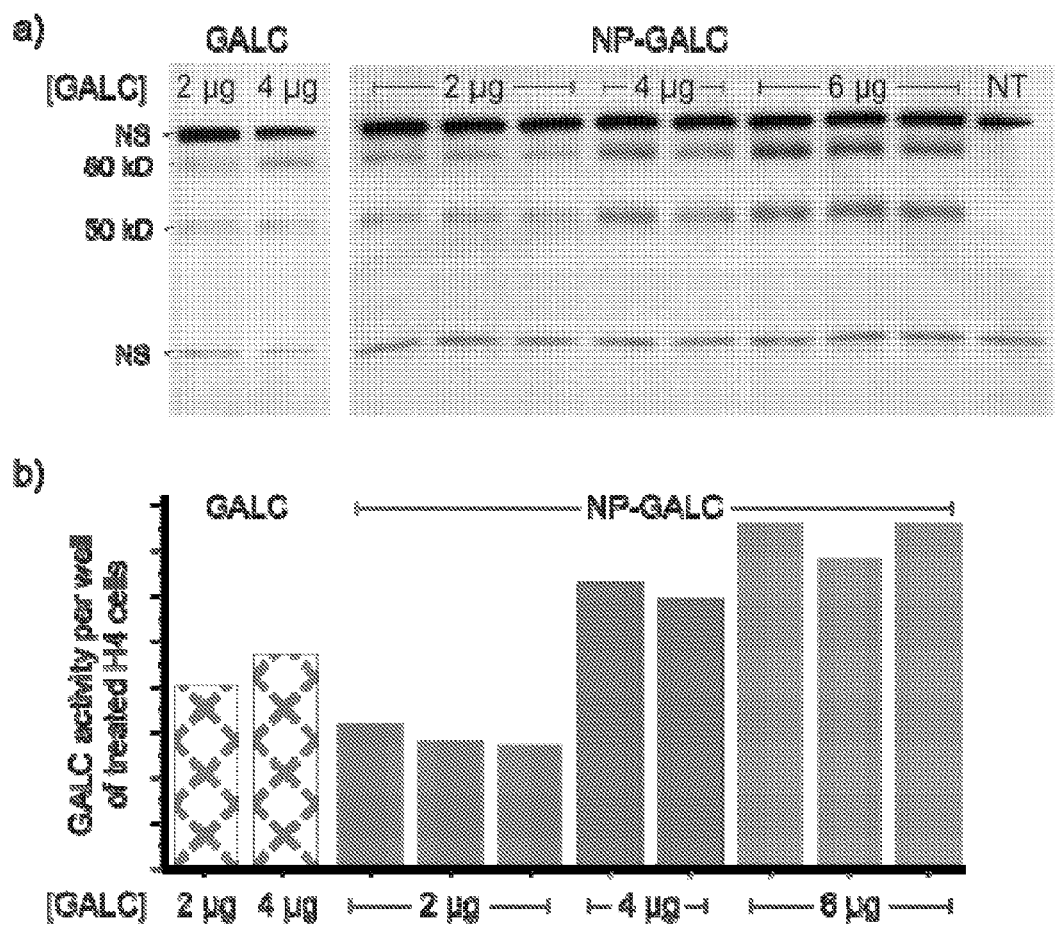
FIG. 2 contains the results of Western blot and GALC activity analysis. (A) Western blot analysis of H4 cell lysates after GALC or NP-GALC treatment and uptake. 40 µg of total protein was loaded per lane and blots were probed with U1021 primary antibody and anti-chicken IgY secondary antibody with a 1 minute exposure. Both the 80 kDa GALC precursor protein and the 50 kDa processed fragment are detected, indicating that GALC is being shuttled to the lysosome of the H4 cells for normal processing (NT=not treated H4 cells). (B) Corresponding GALC activity assay from the same lysates shown in (A).

To date, this method has reproducibly generated NP-GALC conjugates from small scale preparations with approximately 50% surface coverage of COOH-PEG groups that can be converted to IDA and subsequently bound to GALC. Although the NP concentration per NP-GALC preparation has not been confirmed, or the exact number of GALC molecules conjugated per NP, NP-GALC conjugate solutions contain highly active GALC. Using a gel-based assay or a colorimetric GALC activity assay, individual preparations of NP-GALC had a GALC concentration of 20-40 µg/mL. In addition to GALC maintaining its activity after NP conjugation, it has been demonstrated that NP-GALC conjugates are efficiently taken up by cultured H4 cells (a human neuroglioma cell line). Confluent H4 cells were seeded at 70-80% confluency into 12-well plates for 24 hours. Cells were treated with NP-GALC conjugates at 2, 4, or 6 µtotal GALC, or with an equal concentration of GALC alone for an additional 24 hours. Cell lysates were normalized for total protein concentration and analyzed by Western blot analysis and GALC activity assay (FIG. 2). Western blotting was performed with H4 cell lysates following GALC or NP-GALC treatment and uptake. Both the 80 kDa GALC precursor protein and the 50 kDa processed fragment were detected, indicating that GALC was shuttled to the lysosome of the H4 cells for normal processing. Moreover, it was observed that NP-GALC conjugates were transported into H4 cells at an equal or greater level than GALC alone. Furthermore, NP-GALC conjugates were correctly targeted to the lysosome of the cell, which is the site in the cell where GALC is processed from its 80 kDa form into its much more active 50 and 30 kDa fragments, as detected by Western blot. These preliminary experiments demonstrated the biocompatibility of NP-GALC conjugates and the potential for using such conjugates as a form of ERT. Initial data were highly promising and supported the advancement for using polymeric nanoparticle technology for treating CNS disorders.

Example 3

In Vitro and In Vivo Characterization of NP-GALC Conjugates

Preliminary experiments have led to the reproducible generation of NP-GALC conjugates, assembled from a mixture of COOH-PEG-PLA and methoxy-PEG-PLA polymers, such that approximately 50% of the NP surface should be covered with—COOH moieties and available for GALC conjugation. The morphology and size of the NP-GALC conjugates have been estimated by atomic force microscopy (AFM), and the activity of conjugated GALC verified. To better pinpoint the amount of GALC bound per NP, to more accurately calculate the specific activity of the preparations, and to determine general storage conditions that enable optimal stability, in vitro and in vivo characterization of NP-GALC conjugates was performed. AFM was used to calculate the number of NPs present per prepared suspension. Briefly, 10 µL of NP suspension at a wide range of dilutions (10-10,000-fold) were incubated on freshly prepared mica stubs that have been modified with 3'-(aminopropyl)-triethoxysilane (APTES) until the sample spot has dried. A Nanoscope III controller with a Multimode AFM (Veeco Instruments, Inc.) set to ambient tapping mode was used to count the number of NPs (≥10 µm) deposited on an average of ten sectors over a 100 µm$^2$ area. GALC was added to NP preparations at 10 µg/mL. After successive rounds of centrifugation (washing), supernatant layers were concentrated and analyzed alongside the final, 4-fold concentrated, NP-GALC solutions by SDS-PAGE gel electrophoresis. Nearly all of the GALC added had bound to NPs; which correlates well with the estimated amount of GALC, 20-40 µg/mL, based on NP-GALC activity measurements.

Figure 3:
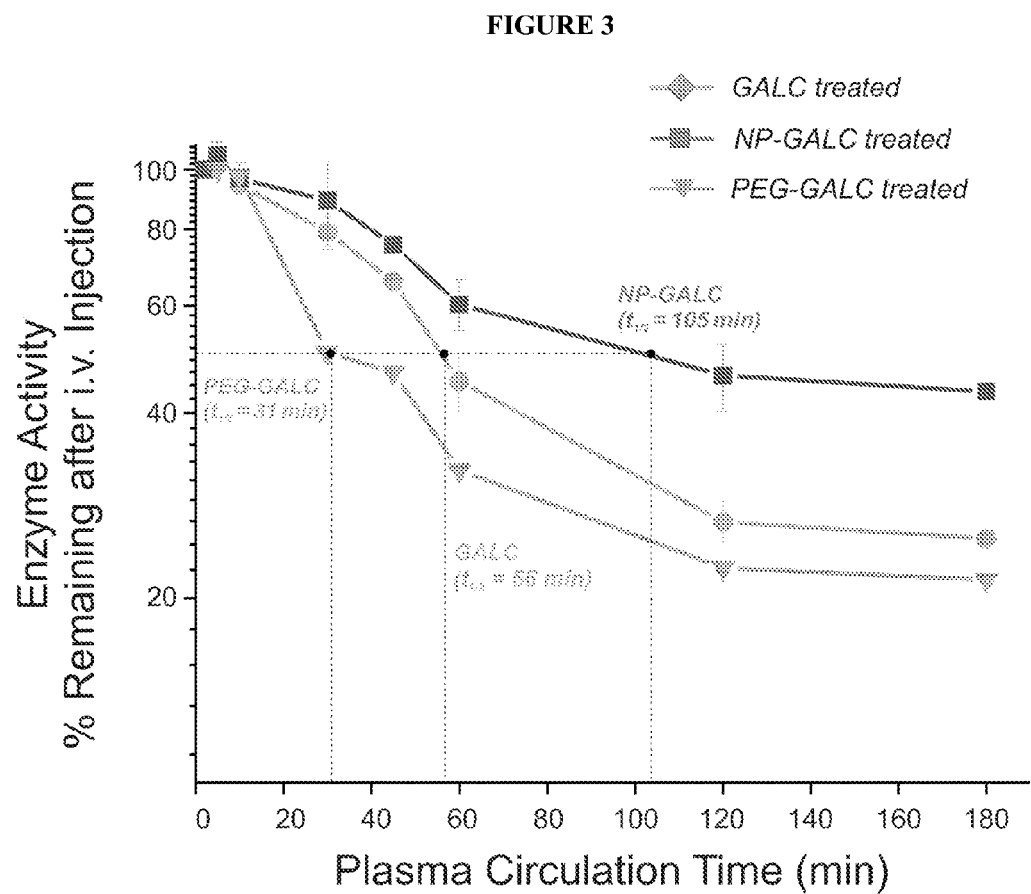
FIG. 3 contains the results of a pharmacokinetics study of GALC lifetime in the blood. Time points indicate how long after tail vein intravenous injection of GALC that the blood was harvested. Approximate $t_{1/2}$ values are indicated.
Figure 4:
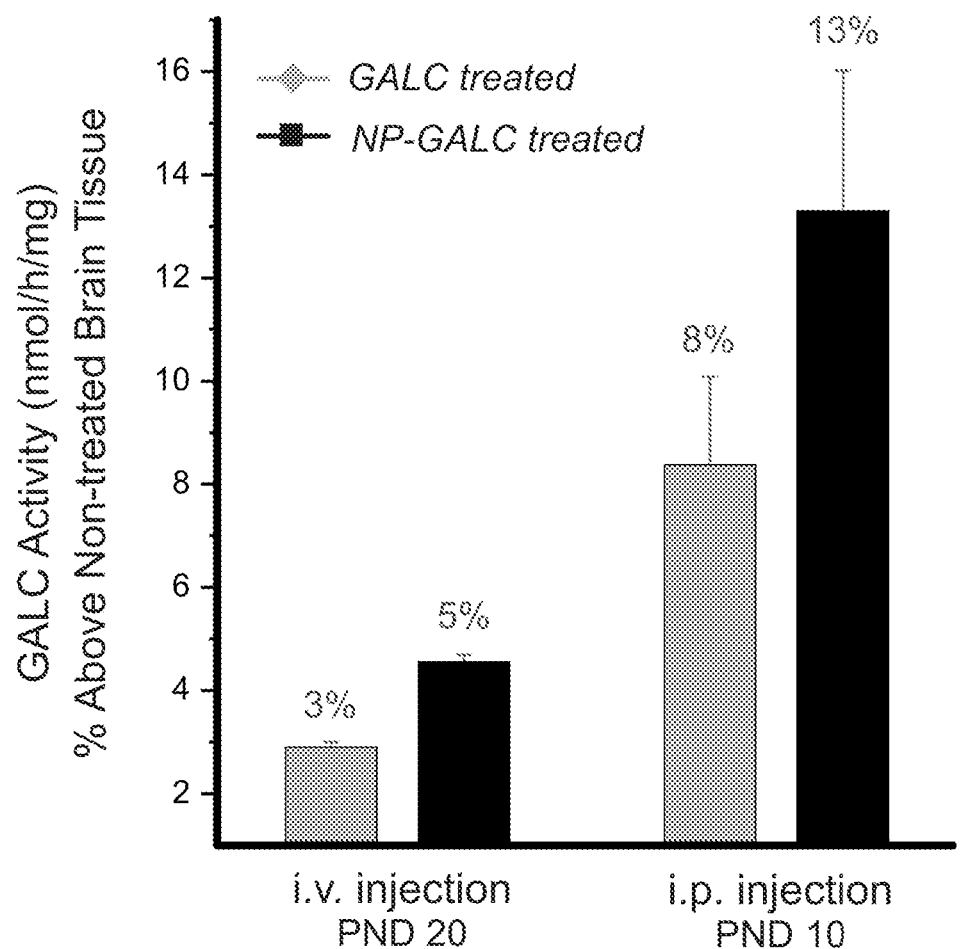
FIG. 4 contains plots of brain GALC levels after GALC or NP-GALC dosing. GALC was administered at 2 mg/kg every other day by either intravenous tail vein injection or i.p. injection. The volume administered (in µL) never exceeded 5 times the mouse body weight (in grams). Brain tissue was harvested at post-natal day 39, 24 hours after the last injection. Tissue was homogenized, normalized for protein levels, and used to assay for enzyme activity.

A pharmacokinetics study was performed to determine the lifetime of GALC in the blood. To determine the plasma half-life ($t_{1/2}$) for GALC, GALC was administered to CD-1 mice by tail vein intravenous injection. Blood was harvested at time points between 0 and 180 minutes following i.v. tail vein injection of GALC. Results indicated that the half-life of GALC in the blood after intravenous injection is approximately 60 minutes (FIG. 3). The half-lives of NP-GALC and PEG-GALC were approximately 105 and 31 minutes, respectively. These methods can be used to perform pharmacokinetic studies on GALC and NP-GALC using intravenous dosing. As demonstrated in FIG. 4, brain GALC activity was measured following i.v. or i.p. injection dosing of GALC or NP-GALC.

Example 4

TIMP-1 Nanoparticles

Figure 5:
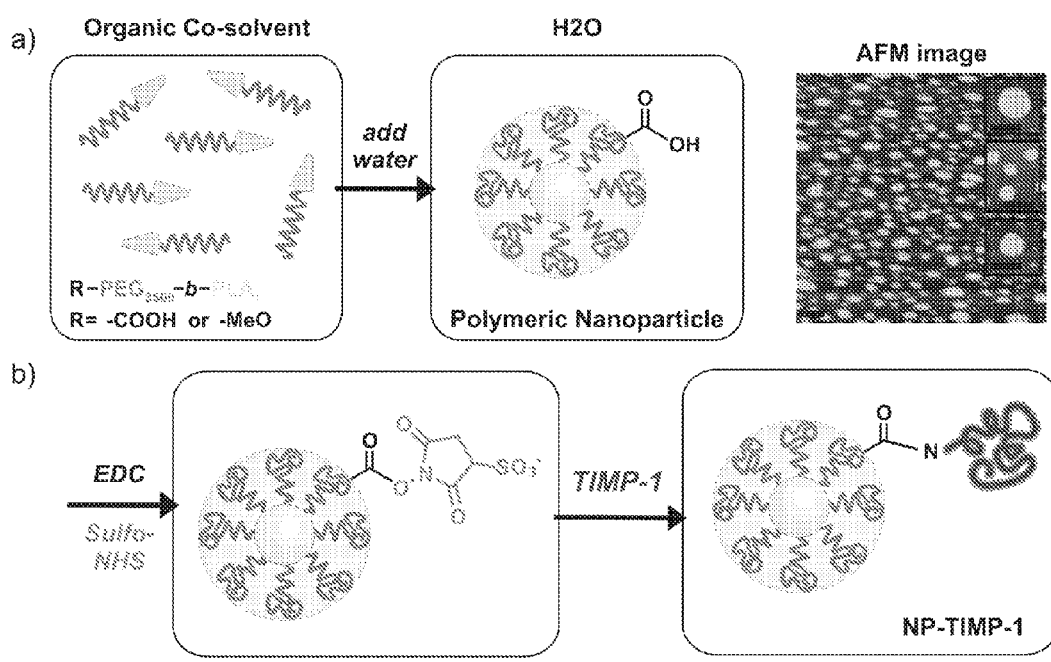
FIG. 5 depicts a slightly modified strategy for covalent attachment of TIMP-1 to the NP surface.
Figure 6:
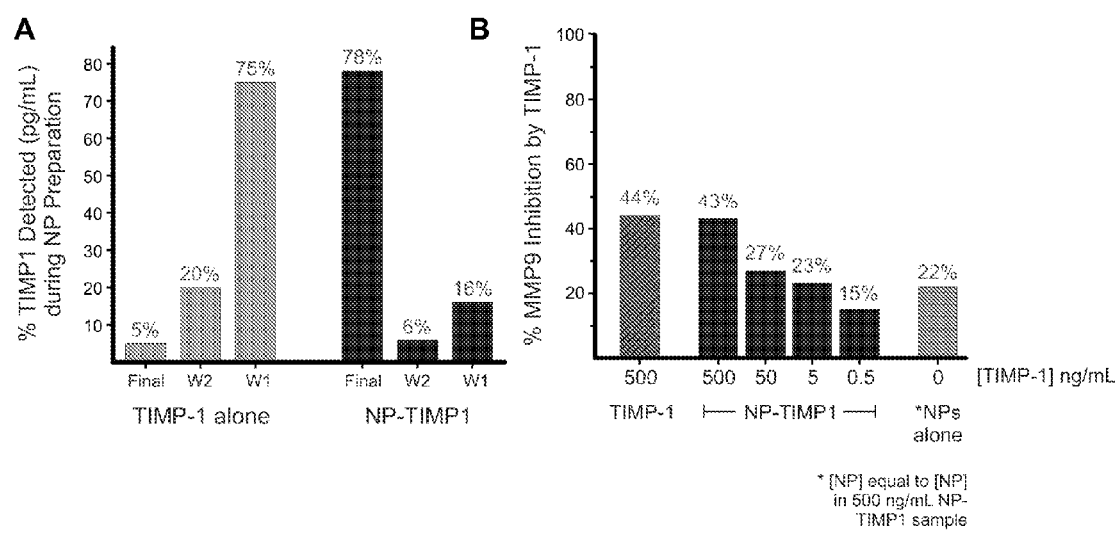
FIG. 6 contains the results of TIMP-1 enzymatic activity assays. (A) Percent of TIMP-1 detected during the washing steps of TIMP-1 attachment to the NP surface. In the absence of NPs, no TIMP-1 is concentrated during centrifugation and dialysis. (B) TIMP-1 inhibitory activity after NP attachment. NP-TIMP1 activity corresponds directly with TIMP-1 activity against MMP9 inhibition.

To test the enzymatic activity of polypeptides following nanoparticle attachment, the polypeptide inhibitor TIMP-1 was conjugated to the surface of polymeric nanoparticles. For nanoparticle assembly, TIMP-1 was added to nanoparticle preparations at a concentration suitable to functionalize ½ of the available sites on the nanoparticle surface. TIMP-1 was covalently linked (via its amine groups) to carboxylic acid moieties on the nanoparticles using NHS-induced bioconjugation chemistry (FIG. 5). TIMP-1 concentration after nanoparticle attachment was detected using a colorimetric, sandwich ELISA assay for TIMP-1. As demonstrated in FIG. 6A, conjugation efficiency was routinely >75%, based on the concentration of TIMP-1 measured during NP-TIMP1 purification. It was observed that TIMP-1 retained its inhibitory activity after attachment to the nanoparticles, as evidenced by inhibition of MMP-9, its natural protein substrate. Furthermore, the NP-TIMP-1 conjugates inhibited MMP-9 in a dose-dependent manner (FIG. 6B). Nanoparticles alone did not exhibit MMP-9 inhibitory activity.

Example 5

Nanoparticle Conjugation of TIMP-1, Sulfamidase, and Arylsulfatase A

To test the enzymatic activity of polypeptides following nanoparticle attachment, the following polypeptides were conjugated to the surface of polymeric nanoparticles: TIMP-1, sulfamidase (SGSH), and arylsulfatase A (ARSA). TIMP-1 was covalently linked to either COOH— or $NH_2$-functionalized nanoparticles. Sulfamidase was covalently linked through COOH— moieties on the nanoparticle surface. Arylsulfatase A was covalently linked via COOH— groups on the nanoparticle surface. Due to differences in protein structure, steric hindrance, and protein dynamics, different proteins will conjugate to the nanoparticle surface at unique rates and at varying concentrations. Accordingly, conjugation conditions for each protein were determined empirically, using a standard nanoparticle preparation procedure. For each conjugation, 20 milligrams (mg) of total polymer were used for batch nanoparticle self-assembly: about 15 mg (75%) had available functional groups (COOH— and $NH_2$) and about 5 mg had unreactive terminal ends (e.g., MeO—). Nanoparticles self-assembled in a final aqueous volume of 10 mL of water or buffered solution. The preparation conditions of each conjugation are summarized in Table 1. Tables 1 and 2 demonstrate that different protein concentrations were required to obtain nanoparticles without a significant loss of enzymatic activity following conjugation. GALC conjugated to the nanoparticle surface at the highest concentration, while TIMP-1 attached to the nanoparticle surface at lower concentrations.

TABLE 1

Polypeptide Conjugation Protocols to Achieve >80% Polypeptide Recovery Without Loss of Enzymatic Activity

| Protein | Concentration | Attachment Chemistry | Preparation Notes |
|---------|---------------|----------------------|-------------------|
| GALC    | 1 mg          | COOH—                | Complete conjugation in less than 2 hours |
| ARSA    | 600 µg        | COOH—                | Conjugation at 4C for 48 hours |
| SGSH    | 500 µg        | COOH—                | Conjugation at 4C for 48 hours |
| TIMP-1  | 100 µg        | COOH—                | Complete conjugation in less than 2 hours |
|         | 20 µg         | $NH_2$—              | Complete conjugation in less than 15 minutes |

TABLE 2

Protein Concentrations Yielding Nanoparticles Without Loss of EnzymaticActivity

| Protein | Activity After Conjugation |
|---------|----------------------------|
| GALC (1 mg) | 100% |
| ARSA (600 µg) | 100% |
| SGSH (500 µg) | 100% |
| TIMP-1 (100 µg; COOH—) | 100% |
| (20 µg; $NH_2$—) | 100% |

Example 6

Immune Response to Nanoparticle Conjugates

Figure 7:
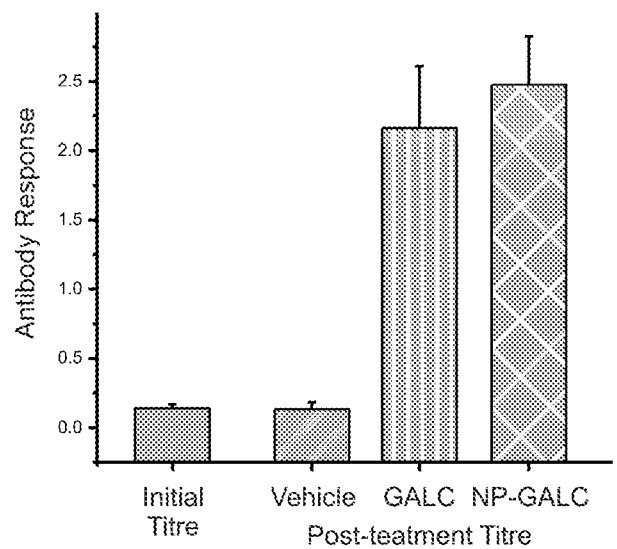
FIG. 7 contains the results of NP-GALC immunogenicity assays. Antibody titers were measured in plasma using ELISA-based assays. Animals (CD-1 mice) were dosed weekly with 10 mg/kg GALC or NP-GALC using tail vein intravenous administration.

To test the immunogenicity of nanoparticle conjugates, mice (n=8) were administered GALC or NP-GALC. CD-1 mice were dosed weekly with 10 mg/kg GALC or NP-GALC using tail vein i.v. administration. The presence of an antibody response was assayed prior to and following a 6-week dosing regimen with GALC alone and NP-GALC conjugates. Antibody titers were measured in plasma using ELISA-based assays. As shown in FIG. 7, no significant difference in immunogenicity was noted between enzyme alone and NP-enzyme-treated animals. These data suggest that nanoparticle-enzyme conjugates do not trigger immunogenicity to a significantly greater extent than enzyme administrated alone.

Example 7

Stability Analysis of Nanoparticle Conjugates

Figure 8:
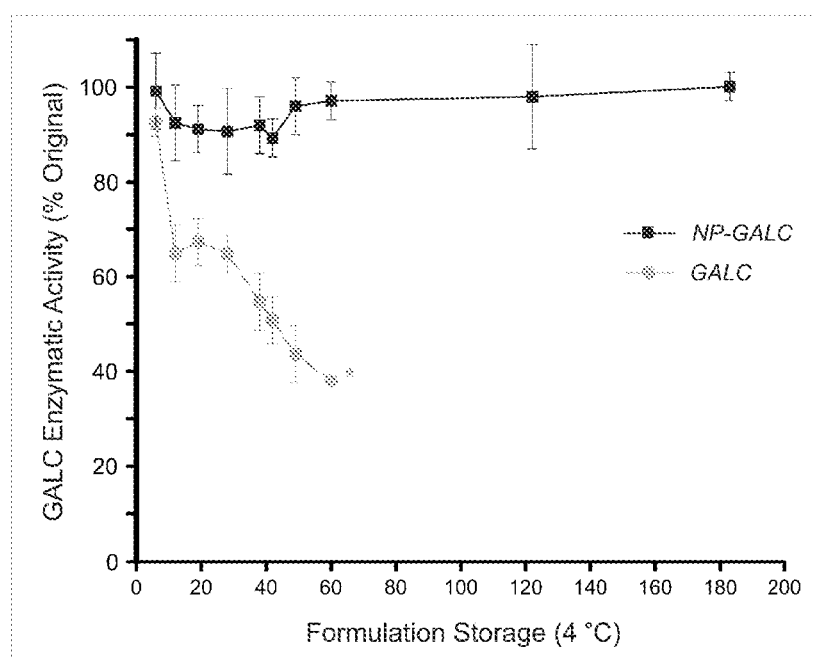
FIG. 8 contains the results of stability analysis of NP-GALC and GALC alone under dry storage at 4° C. Enzyme activity was periodically tested up to 6 months after enzyme formulations were prepared. (*) GALC activity became undetectable sometime between 60 and 120 days, while NP-GALC activity maintained 100% activity for the duration of the study.

To test the stability of stored nanoparticle-enzyme conjugates, a stability analysis was performed. NP-GALC was obtained as described above. NP-GALC and GALC were lyophilized (freeze-dried) and dry stored as lyophilates at 4° C. Enzyme activity of NP-GALC and GALC alone was periodically tested up to 6 months after enzyme formulations were prepared. As shown in FIG. 8, GALC activity became undetectable sometime between 60 and 120 days, while NP-GALC activity maintained 100% activity for the duration of the study. These data suggest that nanoparticle-enzyme conjugates are more stable under these storage conditions than lyophilized enzyme alone.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the serum half-life of an enzymatic polypeptide, wherein said method comprises;
   attaching said enzymatic polypeptide to a polymeric nanoparticle to form a complex,
   wherein said attached enzymatic polypeptide has a longer serum half-life than a control enzymatic polypeptide not attached to a polymeric nanoparticle, wherein said enzymatic polypeptide is attached to said polymeric nanoparticle via one or more attachment points, and
   wherein said polymeric nanoparticle is in the form of a micelle; wherein said enzymatic polypeptide is selected from the group of polypeptides consisting of: a galactocerebrosidase, beta-glucosidase, ceramidase, alpha-L-iduronidase, maltase, sphingomyelinase, hexosaminidase, sulfamidase, and arylsulfatase A;
   wherein said polymeric nanoparticle is assembled from COOH-PEG-PLA, methoxy-PEG-PLA polymers, or maleimide-PEG-PLA polymers, or any combination thereof; and
   wherein said one or more attachment points is independently a N-terminus, a C-terminus, or a tag on the side chain of said enzymatic polypeptide.

2. The method of claim 1, wherein said enzymatic polypeptide attached to said polymeric nanoparticle has at least 85 percent of the level of enzymatic activity of said control enzymatic polypeptide not attached to a polymeric nanoparticle.

3. The method of claim 1, wherein said enzymatic polypeptide attached to said polymeric nanoparticle has at least 95 percent of the level of said enzymatic activity of said control enzymatic polypeptide not attached to a polymeric nanoparticle.

4. The method of claim 1, wherein said enzymatic polypeptide attached to said polymeric nanoparticle has the same level of said enzymatic activity of said control enzymatic polypeptide not attached to a polymeric nanoparticle.

5. The method of claim 1, wherein said enzymatic polypeptide is attached to said polymeric nanoparticle via a covalent bond.

6. The method of claim 1, wherein said enzymatic polypeptide is attached to said polymeric nanoparticle via a non-covalent bond.

7. The method of claim 1, wherein said method comprises lyophilizing said complex to form a lyophilized complex.

8. A method for increasing the stability of enzymatic activity during storage of an enzymatic polypeptide, wherein said method comprises;
   attaching said enzymatic polypeptide to a polymeric nanoparticle to form a complex, wherein said attached enzymatic polypeptide has greater stability of said enzymatic activity during storage than a control enzymatic polypeptide not attached to a polymeric nanoparticle,
   wherein said enzymatic polypeptide is attached to said polymeric nanoparticle via one or more attachment points, and
   wherein said polymeric nanoparticle is in the form of a micelle; wherein said enzymatic polypeptide is selected from the group of polypeptides consisting of: a galactocerebrosidase, beta-glucosidase, ceramidase, alpha-L-iduronidase, maltase, sphingomyelinase, hexosaminidase, sulfamidase, and arylsulfatase A;
   wherein said polymeric nanoparticle is assembled from COOH-PEG-PLA, methoxy-PEG-PLA polymers, or maleimide-PEG-PLA polymers, or any combination thereof; and wherein said one or more attachment points is independently a N-terminus, a C-terminus, or a tag on the side chain of said enzymatic polypeptide.

9. The method of claim 8, wherein said enzymatic polypeptide attached to said polymeric nanoparticle has at least 85 percent of the level of said enzymatic activity of said control enzymatic polypeptide not attached to a polymeric nanoparticle.

10. The method of claim 8, wherein said enzymatic polypeptide attached to said polymeric nanoparticle has at least 95 percent of the level of said enzymatic activity of said control enzymatic polypeptide not attached to a polymeric nanoparticle.

11. The method of claim 8, wherein said enzymatic polypeptide attached to said polymeric nanoparticle has the same level of said enzymatic activity of said control enzymatic polypeptide not attached to a polymeric nanoparticle.

12. The method of claim 8, wherein said enzymatic polypeptide is attached to said polymeric nanoparticle via a covalent bond.

13. The method of claim 8, wherein said enzymatic polypeptide is attached to said polymeric nanoparticle via a non-covalent bond.

14. The method of claim 8, further comprising lyophilizing said complex to form a lyophilized complex.

15. The method of claim 1, wherein the tag is a His6 tag.

16. The method of claim 8, wherein the tag is a His6 tag.

17. The method of claim 1, wherein said enzymatic polypeptide is a galactocerebrosidase polypeptide.

18. The method of claim 8, wherein said enzymatic polypeptide is a galactocerebrosidase polypeptide.

19. The method of claim 1, wherein the enzymatic polypeptide is absent or dysfunctional in lysosomal storage disorders.

* * * * *